United States Patent

Itoh

[11] Patent Number: 5,851,397
[45] Date of Patent: Dec. 22, 1998

[54] AUXILIARY APPARATUS FOR SAMPLING BLOOD SERUM

[76] Inventor: Teruaki Itoh, 5-25 Kokaihommachi, Kumamoto, Japan

[21] Appl. No.: 850,008

[22] Filed: May 1, 1997

[30] Foreign Application Priority Data

May 9, 1996 [JP] Japan .................................... 8-114967

[51] Int. Cl.⁶ .............................. B01D 21/26; G01N 1/00
[52] U.S. Cl. .......................... 210/517; 210/516; 210/518
[58] Field of Search .................................. 210/85, 86, 97, 210/103, 104, 516, 518, 517, 782, 789; 422/100; 435/2; 436/177, 180

[56] References Cited

U.S. PATENT DOCUMENTS

| | | | |
|---|---|---|---|
| 593,333 | 11/1897 | Park | 210/518 |
| 1,240,360 | 9/1917 | Palmer | 210/516 |
| 1,475,985 | 12/1923 | Coffman | 210/517 |
| 1,528,480 | 3/1925 | Henderson | 210/516 |
| 3,879,295 | 4/1975 | Glover et al. | 210/516 |
| 3,890,237 | 6/1975 | Welch | 210/516 |
| 3,929,646 | 12/1975 | Adler | 210/516 |
| 4,142,668 | 3/1979 | Lee | 210/516 |
| 4,326,959 | 4/1982 | Ferrara | 210/516 |
| 4,487,696 | 12/1984 | Ferrara | 210/516 |
| 5,308,506 | 5/1994 | McEwen et al. | 210/516 |

*Primary Examiner*—John Kim
*Attorney, Agent, or Firm*—Nixon & Vanderhye

[57] ABSTRACT

An auxiliary apparatus for sampling blood serum according to the invention comprises a disklike flattening member having a flat surface and capable of flattening a separation surface of a blood serum separating medium contained in a sample container by urging the flat surface against the separation surface, a mounting member having a cylindrical shaft for lowering the flattening member through the blood serum contained in the sample container to thereby mount the flattening member in the sample container such that the flat surface of the flattening member horizontally urges the separation surface of the blood serum separating medium, and means for securing a space which permits a sampling/dispensing tip capable of sampling and dispensing the blood serum, to be inserted into the sample container, by detaching the cylindrical shaft from the flattening member and taking the cylindrical shaft out of the sample container, after the flattening member is mounted in the sample container by the mounting member.

1 Claim, 5 Drawing Sheets

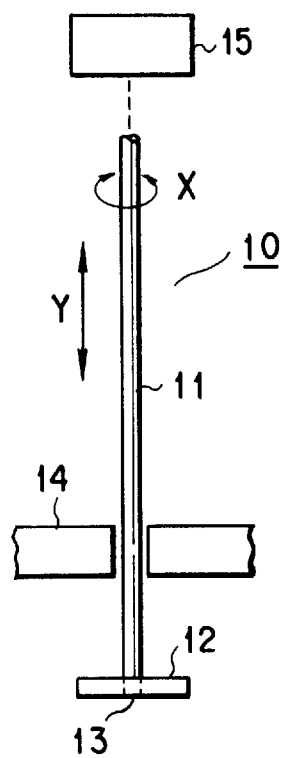
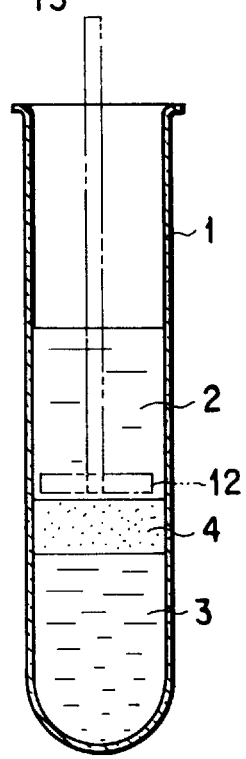
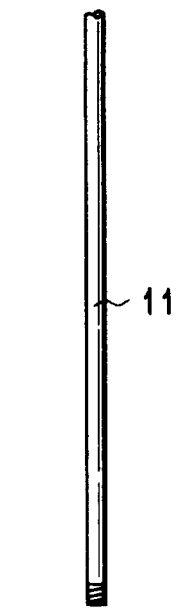
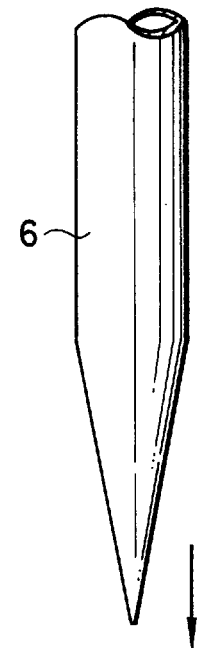
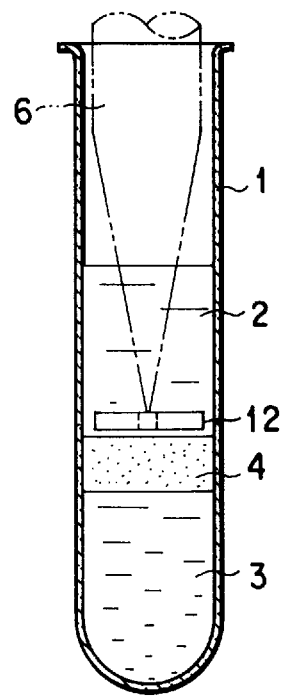
F I G. 1      F I G. 2      F I G. 3

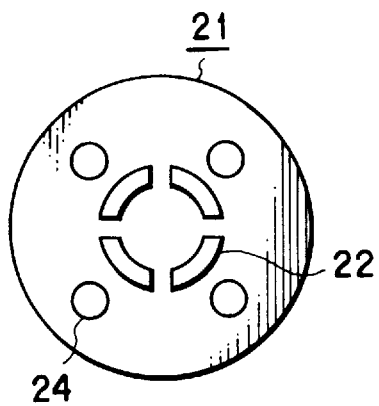
F I G. 4
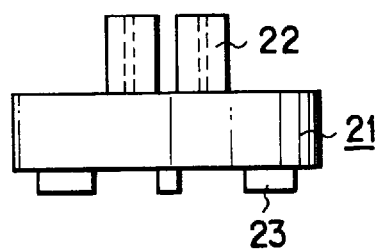
F I G. 5
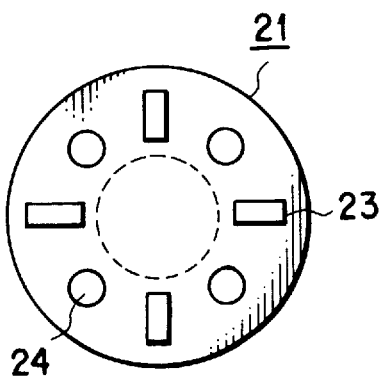
F I G. 6
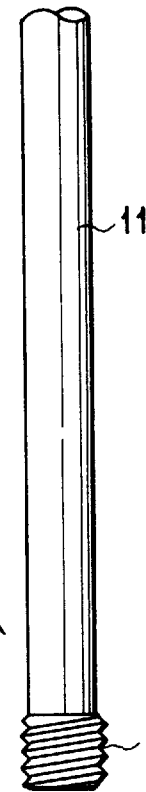
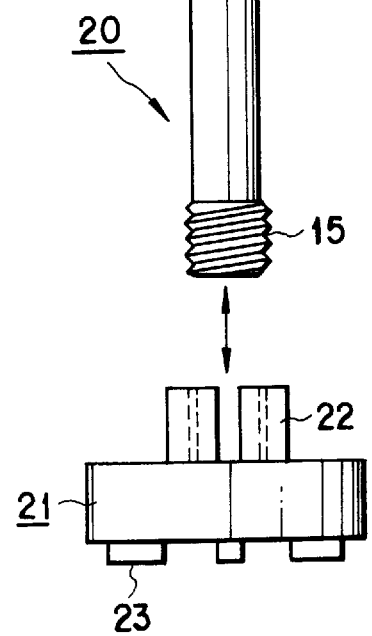
F I G. 7

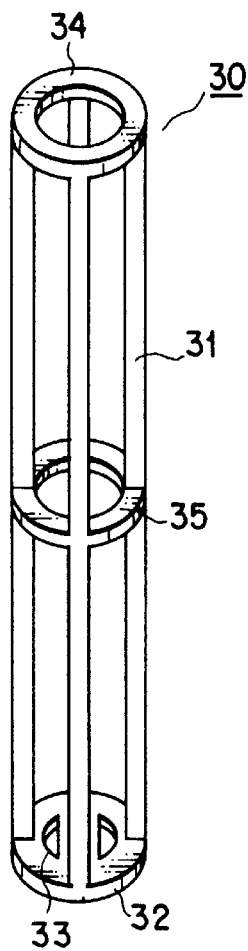
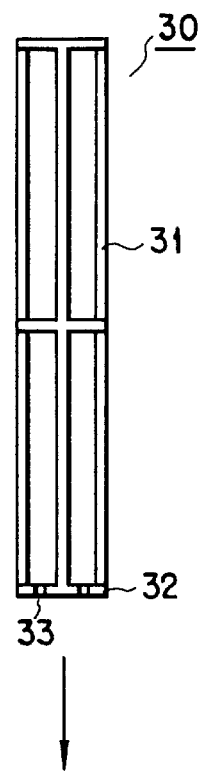
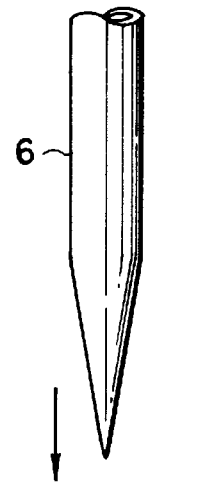
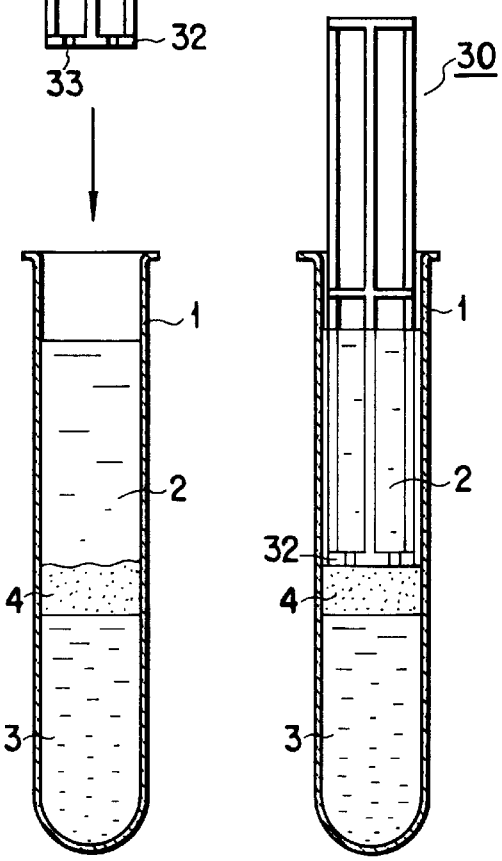
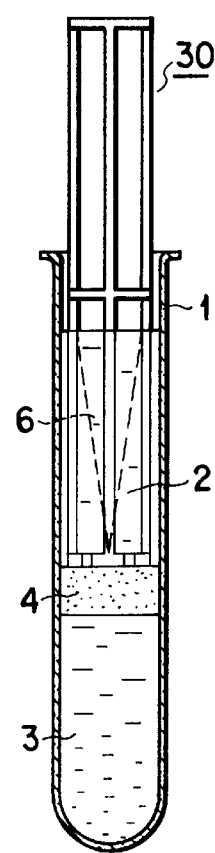
F I G. 8    F I G. 9    F I G. 10    F I G. 11

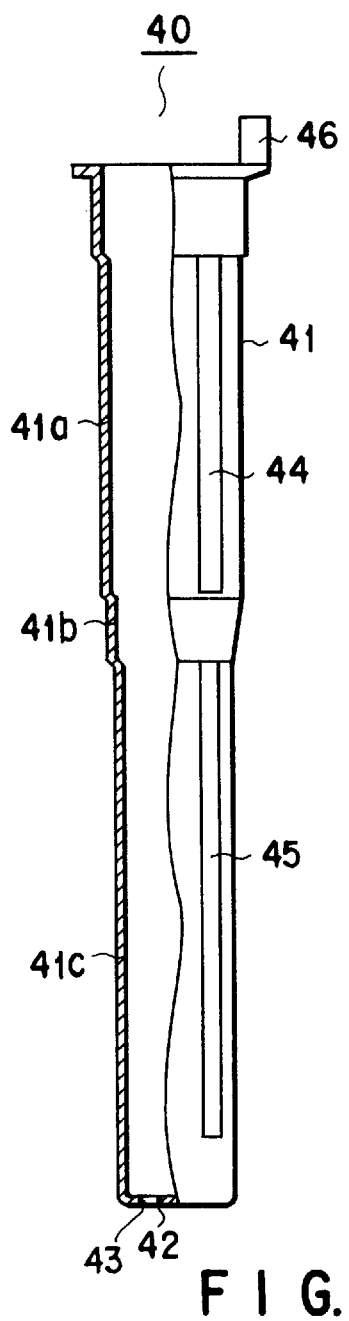
F I G. 12
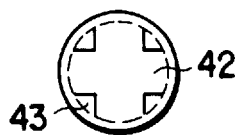
F I G. 13
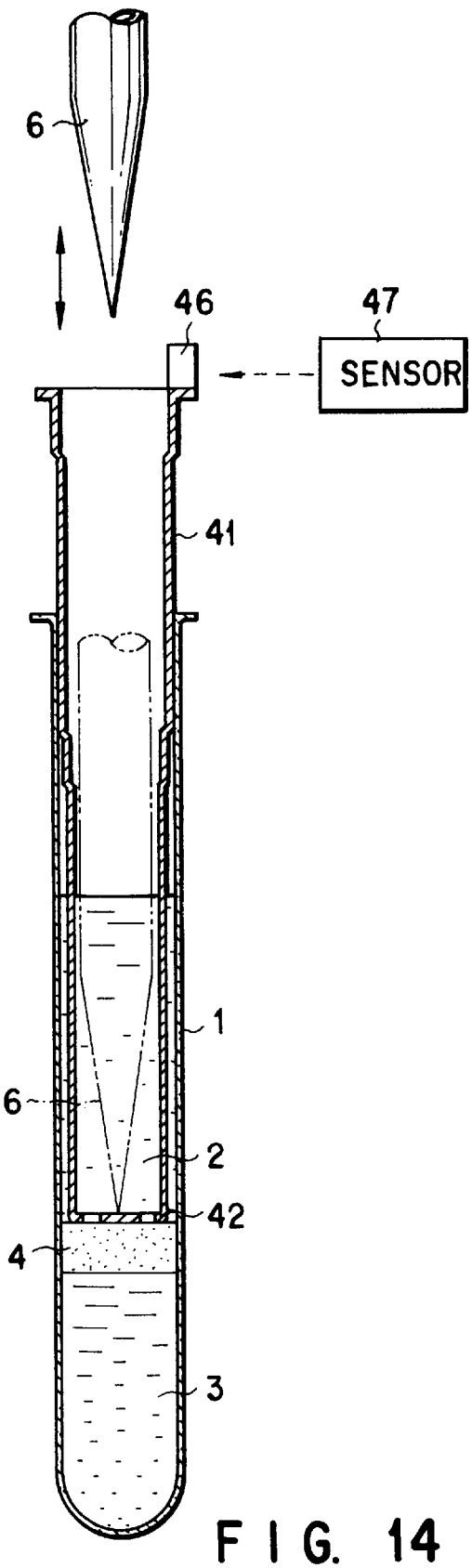
F I G. 14

AUXILIARY APPARATUS FOR SAMPLING BLOOD SERUM

BACKGROUND OF THE INVENTION

This invention relates to an auxiliary apparatus to be used at the time of sampling only blood serum from a centrifuged blood sample.

Before performing various types of blood tests such as a biochemical analysis, etc., blood contained in a specimen container such as a test tube is subjected to a centrifugal treatment, and then blood serum contained therein is sampled and dispensed into several test vessels.

In general, the centrifuged blood sample in a test tube is definitely separated into blood serum and a blood clot by means of a separating medium such as silicon. More specifically, in the test tube, the centrifuged blood sample is separated into the blood serum, the separating medium and the blood clot arranged in this order from above.

To sample the blood serum in the test tube, a sampling/dispensing tip with a sharply tapered, hollow and conical tip portion is inserted into the test tube from above. When the tip portion reaches the blood serum, the tip sucks only the blood serum using an air sucking mechanism, etc., and then is raised and kept at a raised position.

After the sampling operation, the sampling/dispensing tip is shifted to a predetermined position, where the blood serum contained therein is discharged (i.e. dispensed) into several predetermined test vessels.

The blood sample components (i.e. the blood serum, the blood clot, the separating medium) contained in the test tube after the centrifugal treatment do not always show clearly separated states, but may show abnormal states.

FIGS. 15 to 17 show such abnormal states of blood sample components (blood serum 2, a blood clot 3, a separating medium 4) contained in a test tube 1. FIG. 15 shows a case where the separating medium 4 has a separation surface A with irregularities, which contacts the blood serum 2. FIG. 16 shows a case where a separation surface B inclines by a certain angle relative to the axis O of the test tube 1. FIG. 17 shows a case where the separation surface of the separating medium 4 is relatively flat and horizontal, and fibrin 5 which may cause clogging of a sampling/dispensing tip (not shown) is floating in the blood serum 2.

When the separating medium 4 assumes a state as shown in FIGS. 15 or 16, the level at which the separation surface of the separating medium 4 is formed cannot definitely be determined. In other words, the level of the separation surface of the separating medium 4 or that of a deepest portion of the blood serum 2 will assume different values when it is sensed by a sensor (not shown), etc. several times. If the sampling/dispensing tip is lowered to a tip insertion limit set on the basis of such an indefinite sensed level, a lower open end portion of the tip may well thrust into the separating medium 4 and be clogged with the medium.

To avoid this, the prior art takes a measure, for example, to set the tip insertion limit to a level much shallower than the sensed level. This measure, however, makes it impossible to sample all blood serum 2 in the test tube 1, and inevitably limits the effective use of valuable blood serum obtained by a centrifugal treatment.

On the other hand, in the case of FIG. 17 where fibrin is floating in the blood serum 2, the fibrin may be sucked into the open end of the sampling/dispensing tip to thereby clog the same. As a result, it is possible that clogging of the tip will start immediately after the sampling of the blood serum 2. In this case, the aforementioned measure to set the insertion limit of the tip to a much shallower level is quite useless.

BRIEF SUMMARY OF THE INVENTION (a) It is an object of the invention to provide an auxiliary apparatus for sampling blood serum, capable of horizontalizing and flattening, at the time of sampling blood serum, the separation surface of a separating medium easily and accurately, thereby preventing inappropriate setting of the insertion limit of a sampling/dispensing tip due to the fact that the separation surface is not horizontal and/or flat.

(b) It is another object of the invention to provide an auxiliary apparatus for sampling blood serum, capable of preventing a lower open end portion of a sampling/dispensing tip from thrusting into a separating medium even when the lower open end portion of the tip is lowered to a deepest portion of the blood serum, thereby preventing clogging of the tip due to the separating medium and hence enabling sampling of almost all the blood serum contained in the sample container.

(c) It is a further object of the invention to provide an auxiliary apparatus for sampling blood serum, capable of preventing clogging of a sampling/dispensing tip with fibrin.

To attain the above objects, the invention includes the following aspects:

(1) According to a first aspect of the invention, there is provided an auxiliary apparatus for sampling blood serum, comprising:

a flattening member having a flat surface and capable of flattening a separation surface of a blood serum separating medium contained in a sample container by urging the flat surface against the separation surface;

a mounting member for lowering the flattening member through the blood serum contained in the sample container to thereby mount the flattening member in the sample container such that the flat surface of the flattening member horizontally urges the separation surface of the blood serum separating medium; and means for securing a space which permits a sampling/dispensing tip capable of sampling and dispensing the blood serum, to be inserted into the sample container, after the flattening member is mounted in the sample container by the mounting member.

(2) According to a second aspect of the invention, there is provided an auxiliary apparatus for sampling blood serum, comprising:

a disklike flattening member having a flat surface and capable of flattening a separation surface of a blood serum separating medium contained in a sample container by urging the flat surface against the separation surface;

a mounting member having a cylindrical shaft for lowering the flattening member through the blood serum contained in the sample container to thereby mount the flattening member in the sample container such that the flat surface of the flattening member horizontally urges the separation surface of the blood serum separating medium; and means for securing a space which permits a sampling/dispensing tip capable of sampling and dispensing the blood serum, to be inserted into the sample container, by detaching the cylindrical shaft from the flattening member and taking the cylindrical shaft out of the sample container, after the flattening member is mounted in the sample container by the mounting member.

(3) Preferably, in the auxiliary apparatus according to the second aspect, the disklike flattening member and the cylindrical shaft are engaged with each other such that the cylindrical shaft can be disengaged from the disklike flattening member by rotating the cylindrical shaft about an axis of the sample container.

(4) Preferably, in the auxiliary apparatus according to item (3), the disklike flattening member has a rotation stopper projection on the flat surface to be brought into contact with the separating medium.

(5) According to a third aspect of the invention, there is provided an auxiliary apparatus for sampling blood serum, comprising:

a disklike flattening member having a flat surface and capable of flattening a separation surface of a blood serum separating medium contained in a sample container by urging the flat surface against the separation surface; and a mounting member formed, in a cylindrical frame shape, integral with the flattening member, the mounting member being lowered through the blood serum contained in the sample container to thereby mount the flattening member in the sample container such that the flat surface of the flattening member horizontally urges the separation surface of the blood serum separating medium;

wherein the mounting member in the cylindrical frame shape has a space which permits a sampling/dispensing tip to be inserted into the sample container after the flattening member is mounted in the sample container.

(6) According to a fourth aspect of the invention, there is provided an auxiliary apparatus for sampling blood serum, comprising:

a disklike flattening member having a flat surface and capable of flattening a separation surface of a blood serum separating medium contained in a sample container by urging the flat surface against the separation surface; and a mounting member formed, in a cylindrical frame shape, integral with the flattening member, the mounting member being lowered through the blood serum contained in the sample container to thereby mount the flattening member in the sample container such that the flat surface of the flattening member horizontally urges the separation surface of the blood serum separating medium;

wherein the mounting member in the cylindrical frame shape has a lower end portion with a diameter smaller than any other portion thereof, and also has a space which permits a sampling/dispensing tip to be inserted into the sample container after the flattening member is mounted in the sample container.

(7) Preferably, in the auxiliary apparatus according to the third or fourth aspect, the mounting member in the cylindrical frame shape has a position indicating element at an open end portion thereof.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention FIGS. 1 to 3 are views, useful in describing the structure and operation of an auxiliary apparatus for sampling blood serum according to a first embodiment of the invention;

FIGS. 4 to 7 are views, useful in describing the structure and operation of an auxiliary apparatus for sampling blood serum according to a second embodiment of the invention;

FIGS. 8 to 11 are views, useful in describing the structure and operation of an auxiliary apparatus for sampling blood serum according to a third embodiment of the invention;

FIGS. 12 to 14 are views, useful in describing the structure and operation of an auxiliary apparatus for sampling blood serum according to a fourth embodiment of the invention.

DETAILED DESCRIPTION OF THE INVENTION

First Embodiment

Figures 15, 16, 17:
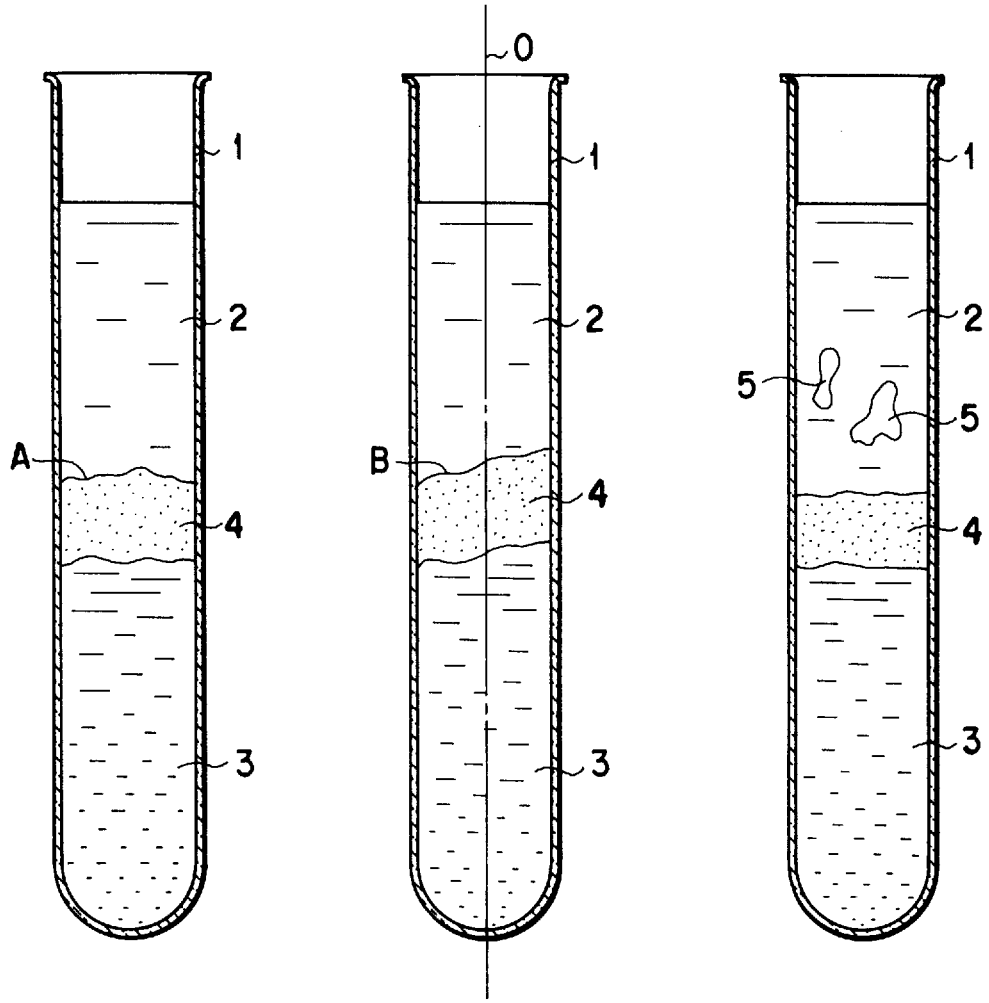
FIGS. 15 to 17 are views, useful in explaining the problems of the prior art and showing examples of blood samples of abnormal states obtained after a centrifugal treatment, respectively.

FIGS. 1 to 3 illustrate the structure and operation of an auxiliary apparatus for sampling blood serum according to a first embodiment of the invention. As is shown in FIG. 1, a blood sample contained in a test tube 1 as a sample container and obtained after a centrifugal treatment is separated into blood serum 2 and a blood clot 3 by means of a separating medium 4 made of silicon, etc. An auxiliary apparatus 10 for sampling the blood serum comprises a cylindrical shaft 11 and a flattening member 12 with a center portion 13 thereof screwed on a lower end portion of the shaft 11. The flattening member 12 is a disk-shaped member, has at least the lower end surface thereof formed flat, and is attached to the shaft 11 vertically with respect to the axis thereof.

The shaft 11 is driven by a driving mechanism 15 formed of an air-piston/cylinder device, etc. such that it is vertically reciprocated as indicated by an arrow Y and rotated about the axis as indicated by an arrow X. A guide member 14 is provided for enabling the shaft 11 to move parallel to the axis of the test tube 1 in a reliable manner.

The shaft 11, the guide member 14, etc. constitute the mounting members of the invention.

At the time of sampling the blood serum 2, the driving mechanism 15 is operated so as to first lower the serum sampling auxiliary apparatus 10. As a result, the shaft 11 and the flattening member 12 are inserted into the test tube 1. When the lower surface of the flattening member 12 reaches the upper surface of the separating medium 4 as indicated by the dotted line in FIG. 1, the auxiliary apparatus 10 is stopped. If necessary, the apparatus 10 is a little further lowered and adjusted such that the flat surface of the flattening member 12 slightly urges the upper surface of the separating medium 4. As a result, the upper surface or separation surface of the separating medium 4 is flattened vertical to the axis of the test tube 1.

Subsequently, the shaft 11 is rotated by the driving mechanism 15 in a predetermined direction, thereby disengaging the shaft 11 from the flattening member 12. After the shaft 11 is separated therefrom, it is taken out of the test tube 1 as shown in FIG. 2. Thus, only the flattening member 12 remains in the test tube 1. When the shaft 11 is taken out of the test tube 1, a space for inserting therein a sampling/dispensing tip 6 (the space is filled with blood serum) is defined above the flattening member 12 is secured.

At this time, a sampling/dispensing mechanism (not shown) is operated, thereby inserting the sampling/dispensing tip 6 into the test tube 1 as indicated by the arrow in FIG. 3 until a lower open end portion of the tip 6 reaches the upper surface of the flattening member 12. The lower open end portion of the tip 6 is ideally fitted in the shaft engagement hole of the center portion 13 of the flattening member 12.

At this time, a suction treatment is performed by the air suction means to suck the blood serum 2 into the sampling/dispensing Tip 6. Thus, the blood serum 2 is sampled. After completion of the sampling of the blood serum 2, the tip 6 is raised by the sampling/dispensing mechanism and then shifted to a predetermined position. In the predetermined position, the sucked blood serum 2 is dispensed into predetermined test containers.

Even if in the apparatus of the first embodiment, the separation surface of the separating medium 4 comes, as a result of the centrifugal treatment, to have irregularities or to incline relative to the axis of the test tube 1, it is pushed by the flat surface of the flattening member 12 during sampling the blood serum 2, and therefore comes flat and perpendicular to the axis of the test tube 1. Accordingly, the level of the separation surface of the separating medium 4 comes definite, and hence can be accurately sensed, for example, by an optical level sensor, etc. Similarly, the degree of insertion of the sampling/dispensing tip 6 can be set appropriately.

Thus, inappropriate setting of the insertion limit of the sampling/dispensing tip 6, which may occur when the separation surface of the separating medium 4 is not flat and/or not horizontal, is prevented. Furthermore, even if in the first embodiment, the tip 6 is lowered such that the lower open end portion thereof reaches the separation surface of the separating medium 4, it is put into contact with the edge of the shaft engagement hole of the center portion 13 of the flattening member 12, or with the upper surface of the flattening member 12. Accordingly, the tip 6 will no more descend and will not thrust into the separating medium 4. This means that the tip is free from clogging due to the medium 4. As a result, the tip 6 can sample almost all the blood serum 2 contained in the test tube 1. In addition, even when fibrin (not shown) is floating in the blood serum 2, it is pushed against the upper surface of the separating medium 4 by the flattening member 12 while the flattening member 12 lowers in the blood serum 2. Since fibrin is thus removed from the blood serum 2, clogging of the sampling/dispensing tip 6 with fibrin is prevented.

In a case where the insertion limit of the sampling/dispensing tip 6 can accurately be controlled, the flattening member 12 may be formed integral with the shaft 11 such that it can be raised together with the shaft 11.

Second Embodiment

FIGS. 4 to 7 are views, useful in describing the structure and operation of an auxiliary apparatus for sampling blood serum according to a second embodiment of the invention. As shown in FIGS. 4 to 7, an auxiliary apparatus 20 for sampling blood serum according to the second embodiment comprises a shaft 11 and a flattening member 21.

The flattening member 21 is a disk-shaped member. The flattening member 21 includes a plurality (four in this embodiment) of coupling members 22, which project from central portions of the member 21 at regular intervals in the form of a circle, and have female screw portions formed in the inner surfaces thereof, respectively, to be engaged with a male screw portion 15 formed on the shaft 11. The flattening member 21 further includes a plurality (four in this embodiment) of rotation stopper projections 23 provided on peripheral portions of the lower surface thereof, and a plurality (four in this embodiment) of through holes 24 extending between the upper and lower surfaces thereof. The other structural elements of the second embodiment are similar to those of the first embodiment, and hence are not described.

The auxiliary apparatus 20 of the second embodiment has advantages as described below, in addition to the aforementioned advantage of the apparatus 10 of the first embodiment. Since the stopper projections 23 of the flattening member 21 bite the upper surface of the separating medium 4 when the apparatus 20 is inserted in the test tube 1, the flattening member 21 is prevented from rotating together with the shaft 11 when the shaft 11 is rotated in a predetermined direction to be separated from the flattening member 21. Thus, the shaft 11 can be detached from the flattening member 21 in an easy and reliable manner. Further, the through holes 24 formed in the flattening member 21 enable the member 21 to be sent to the deepest portion of the blood serum 2 without resistance thereof, since the blood serum 2 is smoothly guided through the holes to the above of the member 21. The coupling members 22 are separated from each other at regular intervals, and hence the blood serum 2 guided above the flattening member 21 smoothly flows between each pair of adjacent ones of the coupling members 22. By virtue of this structure, the overall blood serum can be sucked by the sampling/dispensing tip 6.

Third Embodiment

FIGS. 8 to 11 are views, useful in describing the structure and operation of an auxiliary apparatus 30 for sampling blood serum according to a third embodiment of the invention. As shown in FIG. 8, the auxiliary apparatus 30 for sampling blood serum according to the third embodiment comprises a cylindrical frame member 31 and a disklike flattening member 32 attached to the lower end of the frame member 31. The flattening member 32 is arranged perpendicular to the axis of the test tube 1, and has a flat lower surface. The flattening member 32 further has a plurality (two in this embodiment) of through holes 33 extending between the upper and lower surfaces thereof. Reinforcing rings 34 and 35 are provided at an upper end portion and an intermediate portion of the frame member 31, respectively.

At the time of sampling the blood serum 2, the auxiliary apparatus 30 is inserted into the test tube 1 by means of a driving mechanism (not shown), as is indicated by the arrow in FIG. 9. More specifically, the frame member 31 is inserted into the test tube 1 with its outer peripheral surface kept in substantially tight contact with the inner peripheral surface of the test tube 1. As a result, the upper surface of the separating medium 4 is flattened by the flat surface of the flattening member 32 as shown in FIG. 10. The frame member 31 is a hollow member which has a space for guiding therein the sampling/dispensing tip 6 and the blood serum 2.

The auxiliary apparatus 30 of the third embodiment has advantages as described below, in addition to the aforementioned advantage of the apparatus 10 of the first embodiment. Since the flattening member 32 is formed integral with the frame member 31, it can be positioned perpendicular to the axis of the test tube 1 in a more accurate manner. Moreover, the sampling/dispensing tip 6 is guided into the test tube 1 to perform a sampling operation, with the frame member 31 inserted in the test tube 1, which means that the frame member 31 serves as an insertion guide for inserting the tip 6. Thus, the blood serum 2 can be very smoothly sampled by the sampling/dispensing tip 6 kept at an axial portion of the test tube 1 in a reliable and accurate manner.

Fourth Embodiment

FIGS. 12 to 14 are views, useful in describing the structure and operation of an auxiliary apparatus 40 for sampling blood serum according to a fourth embodiment of the invention. As shown in FIGS. 12 to 14, the auxiliary apparatus 40 of the fourth embodiment comprises a substantially cylindrical frame member 41, a disklike flattening member 42 formed to the lower end of the frame member 41, and a position indicating element 46 formed to an upper open end portion of the frame member 41 and made of e.g. a metal. The frame member 41 has an upper large-diameter portion 41a, an intermediate middle-diameter portion 41b and a lower small-diameter portion 41c, which are formed integral with each other. The large-diameter portion 41a and the small-diameter portion 41c have slits 44 and 45, respectively. The substantially cylindrical frame member 41 is a hollow member and has a space for permitting insertion of the sampling/dispensing tip 6 therein. The flattening member 42 has four through holes 43 extending between the upper and lower surfaces thereof. The position indicating element 46, which projects from the upper open end portion of the frame member 41, can be sensed by a sensor 47 constituted, for example, of a photoelectric element.

At the time of sampling the blood serum 2, the frame member 41 is inserted into the test tube 1 through the opening thereof, and the flattening member 42 passes the blood serum 2 and reaches the upper surface of the separating medium 4. If necessary, the flattening member 42 is a little more pushed downward. At this time, the large-diameter portion 41a is in substantially tight contact with the inner peripheral surface of the test tube 1. As a result, the upper surface of the separating medium 4 is flattened by the flat surface of the flattening member 42 kept perpendicular to the axis of the test tube 1.

In this state, the position indicating element 46 projecting from the upper open end portion of the frame member 41 is sensed by the sensor 47, thereby detecting an insertion limit up to which the sampling/dispensing tip 6 can be lowered. A position signal indicative of the detected insertion limit is supplied to an operation control section (not shown). The operation control section in turn supplies a control signal to the sampling/dispensing mechanism so as to stop the sampling/dispensing tip 6 in a position in which the lower end of the tip 6 approaches the separation surface of the separating medium 4 as close as possible. As a result, the blood serum 2 is reliably sampled.

In addition to the aforementioned advantage of the apparatus 10 of the first embodiment, the auxiliary apparatus 40 of the fourth embodiment is advantageous in that the frame member 41 has a tapered body which comprises the large-diameter portion 41a, the middle-diameter portion 41b and the small-diameter portion 41c, and therefore can be smoothly inserted into the test tube 1.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

I claim:

1. An auxiliary apparatus for sampling blood serum, comprising:

a disklike flattening member having a flat surface and capable of flattening a separation surface of a blood serum separating medium contained in a sample container by urging the flat surface against the separation surface;

a mounting member having a cylindrical shaft for lowering the flattening member through the blood serum contained in the sample container to thereby mount the flattening member in the sample container such that the flat surface of the flattening member horizontally urges the separation surface of the blood serum separating medium; and means for securing a space which permits a sampling/dispensing tip capable of sampling and dispensing the blood serum, to be inserted into the sample container, by detaching the cylindrical shaft from the flattening member and taking the cylindrical shaft out of the sample container, after the flattening member is mounted in the sample container by the mounting member, wherein the disklike flattening member has a rotation stopper projection on the flat surface to be brought into contact with the separating medium and the disklike flattening member and the cylindrical shaft are engaged with each other such that the cylindrical shaft can be disengaged from the disklike flattening member by rotating the cylindrical shaft about an axis of the sample container.

* * * * *